United States Patent
Hashiba et al.

(10) Patent No.: US 6,878,824 B2
(45) Date of Patent: Apr. 12, 2005

(54) PROCESS FOR PREPARING N-METHYLATED MELAMINES

(75) Inventors: Isao Hashiba, Funabashi (JP); Takayuki Tamura, Funabashi (JP); Hiroyuki Kousaka, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 281 days.

(21) Appl. No.: 10/390,706

(22) Filed: Mar. 19, 2003

(65) Prior Publication Data

US 2004/0186289 A1 Sep. 23, 2004

(51) Int. Cl.[7] ............................................. C07D 251/70
(52) U.S. Cl. ....................................................... 544/196
(58) Field of Search ................................. 544/196, 194

(56) References Cited

U.S. PATENT DOCUMENTS 2,228,161 A  1/1941  Zerweck et al. ............ 544/196
4,886,882 A  12/1989  Ebel et al. .................. 544/196
5,124,379 A  6/1992  Cipolli et al. ................ 524/97

FOREIGN PATENT DOCUMENTS

| GB | 496690 | 12/1938 |
|---|---|---|
| JP | A 2003-12654 | 1/2003 |

OTHER PUBLICATIONS

Kaiser et al., "Cyanuric Chloride Derivatives. II. Substituted Melamines", This Journal, vol. 73, pp. 2984–2986, 1951.

*Primary Examiner*—John M. Ford
(74) *Attorney, Agent, or Firm*—Oliff & Berridge, PLC

(57) ABSTRACT

The present invention provides a process for preparing N-methylated melamines in simple steps by using inexpensive raw materials in such a manner that the proportion of mono-type, bis-type and tris-type of the N-methylated melamines as prepared can be controlled. The process comprises reacting by heating melamine with methylamine in the presence of an acidic catalyst under pressure to substitute at least one amino group of the melamine by methylamino group.

12 Claims, No Drawings

PROCESS FOR PREPARING N-METHYLATED MELAMINES

BACKGROUND OF THE INVENTION

1. Field of the Art

The present invention relates to a process for preparing N-methylated melamines characterized by heating melamine (2,4,6-triamino-1,3,5-triazine) with methylamine (monomethylamine) in the presence of an acid catalyst under pressure to substitute at least one amino group of the melamine by methylamino group(s).

Specifically, the reaction of melamine and methylamine in the presence of an acid catalyst leads N-methylated melamines including 2,4-diamino-6-methylamino-1,3,5-triazine (mono-type), 2-amino-4,6-bis(methylamino)-1,3,5-triazine (bis-type) and 2,4,6-tris(methylamino)-1,3,5triazine (tris-type) as desired compounds.

N-methylated melamines are useful compound groups that are used widely as various fine chemical intermediates for agricultural chemicals, medicines, dyes, paints and the like, as forming components for various resin materials, in particular an aminoplast, and as a flame retardant.

2. Description of the Related Art

As methods for preparing N-alkylated melamines, synthetic methods by reacting cyanuric chloride with an alkylamine are reported (J. Amer. Chem. Soc., 73,2984 (1951) and U.S. Pat. Nos. 5,124,379 and 4,886,882). The synthetic methods require expensive cyanuric chloride, a plurality steps for synthesizing mono-type and bis-type of N-alkylated melamines and further disposal of hydrochloric acid in post-treatment.

Further, a synthetic method disclosed in U.S. Pat. No. 2,228,161 (corresponding to GB Patent No. 496,690) is also known. The synthetic method comprises reacting melamine with hydrochloride of an alkylamine. As the reaction requires to be carried out in a state of solid by using hydrochloric acid, an amount of reactants to be treated is very large. In addition, the reaction needs countermeasures against corrosion in an apparatus and lowering in quality of products due to the use of the hydrochloride in a high temperature. Further, the reaction necessitates disposal of hydrochloric acid in post-treatment. The above-mentioned U.S. Pat. No. 2,228,161 discloses a method as a synthetic method of N-methylated melamines in which melamine and methylamine hydrochloride are reacted at 200° C. on a solid phase. The patent publication reports that the yield of 2-amino-4,6-bis(methylamino)-1,3,5-triazine (bis-type) is 50 to 55% N-methylated melamines and that a small amount of 2,4,6-tris(methylamino)-1,3,5-triazine (tris-type) is obtained.

It is known that the yield by a method in which methylol melamine is reduced is low and that the method requires treatment of polymers that are generated as by-product

SUMMARY OF THE INVENTION

The present invention provides a process for preparing N-methylated melamines. In detail, the present invention provides a process for preparing N-methylated melamines that is carried out in simple steps by using melamine and methylamine that are inexpensive raw materials and that can control the proportion of mono-type, bis-type and tris-type in prepared N-methylated melamines.

A first embodiment of the present invention is a process for preparing N-methylated melamines comprising reacting by heating melamine with methylamine in the presence of an acidic catalyst underpressure to substitute at least one amino group of the melamine by methylamino group.

The first embodiment includes the following preferred embodiments:

1) wherein a temperature of 160° to 250° C. is selected as a reaction temperature; and 2) wherein the reaction is carried out with removal of ammonia generated in the course thereof and thereby increasing the proportion of N-methylated melamines of tris-type and bis-type.

A second embodiment of the present invention is a process for preparing N-methylated melamines comprising reacting by heating melamine, methylamine and a solvent in the presence of an acidic catalyst under pressure to substitute at least one amino group of the melamine by methylamino group.

The second embodiment includes the following preferred embodiments:

1) wherein the solvent is one or more of trialkykamines;

2) wherein a temperature of 160° to 250° C. is selected as a reaction temperature; and 3) wherein the reaction is carried out with removal of ammonia generated in the course thereof and thereby increasing the proportion of N-methylated melamines of tris-type and bis-type.

The present invention can provide a process for synthesizing N-methylated melamines by using melamine and methylamine that are inexpensive raw materials. In addition, the present invention enables the proportion of substituted types of N-methylated melamines to control by selecting the amount of methylamine used and carrying out removal of ammonia as generated. In particular, the yield of 2,4,6-tris (methylamino)-1,3,5-triazine (tris-type) exceeds 80%.

Further, as the above-mentioned reaction must be carried out under a high pressure and at a high temperature, the selection of material of reactor used is in problem. However, the present inventors found out that the use of trialkylamines as a solvent can avoid corrosion of reactors in the course of the reaction and the application of high pressure. Consequently, reactors (e.g., an autoclave) are prevented from corrosion, and it makes possible to carrying out the action at a temperature of 190° C. and a pressure of 7 MPa or less although the pressure is selected depending on the amount of solvent used. Accordingly, the present invention permits reactors designated for using under a low pressure to be utilized.

Also, the present invention is excellent in that N-methylated melamines are useful compounds conferring flexibility on melamine resins and that N-methylated melamines have high solubility in water, and mix with melamines optionally and thereby being able to polymerize with formalin.

For example, the conferring of flexibility on melamine resins makes clear from a flex test (Evaluation Example 2 in WO97/11102) in which an impregnated paper is prepared by impregnating a resin solution obtained by adding tris-type resin to melamine resin, the impregnated paper is processed to a laminated cured sheet and the sheet is evaluated.

Melamine resins prepared from melamine are very hard and therefore have brittleness. When flexibility is to be conferred on the melamine resins for improving the brittleness thereof, even a mixture of mono-type, bis-type and tris-type of N-methylated melamines can be used.

DESCRIPTION OF THE PREFERRED EMBODIMENTS

Each of the abovementioned embodiments is specifically described in the followings.

After melamine, an acidic catalyst and a solvent are charged into an autoclave, a bomb charged with methylamine is connected to the autoclave, and the autoclave is cooled with dry ice-acetone refrigerant. Then, methylamine in a state of gas is blown into the autoclave from the bomb while weighing with a balance. After the predetermined amount of methylamine is blown into, charging is completed.

Thereafter, the reaction is carried out at a temperature of 190° C. by heating the autoclave.

The reaction can be carried out at a temperature between 140° C. and 300° C. However, when the temperature is high, side reactions occur and thereby yield lowers, and further reaction pressure increases. A temperature between 160° C. and 250° C. is preferable, and a temperature between 160° C. and 200° C. is more preferable. The reaction is an equilibrium reaction in which methylamine is converted to ammonia, and comes to equilibrium in about 2 hours in a case where the reaction is carried out at 190° C. When ammonia is removed from the reaction system, the equilibrium shifts and the rate of reaction increases more and more.

The proportion of the substituted reaction products can be relatively controlled, and tris-type can be produced in a yield of about 40 to 80%.

The pressure on reaction is 6 to 8 MPa at 170° C. or 11 to 12 MPa at 190° C. in a case where no solvent is used. On the other hand, in a case where solvents are used, for example when trimethylamine is used as a solvent in an amount of 50 parts by weight based on 100 parts by weight of melamine, the pressure is 4 to 6 MPa. It is preferable to use solvents from the viewpoint of the structure of apparatus (reactor) and safety.

The amount of methylamine is 30 to 5000 parts by weight based on 100 parts by weight of melamine. The more methylamine is used, and the more tris-type is produced. On the other hand, the less it is used, and the more mono- or bis-type (low substituted product) is produced. In addition, methylamine acts also as a solvent for dissolving melamine although this depends on the amount of trialkylamines used. Therefore, the rate of reaction makes low when the amount of methylamine is too small.

Instead of methylamine, alkylamines (monoalkylamines) having carbon atoms of 4 or less may be used similarly to methylamine. The reaction pressure makes lower with an increase in carbon atoms of alkylamines, and thereby the treatment of reaction makes easier.

As the acidic catalyst, a salt of a strong acid with a weak base, a salt of a strong acid with a strong base, an acid or the like can be used.

The salt of a strong acid with a weak base includes, for example ammonium chloride (sublimed at 337° C.), ammonium sulfate, ammonium phosphate and the like. Also, a quaternary ammonium salt can be used as an acidic catalyst. Taking into account separation of an acidic catalyst in post-treatment, it is preferable to use a quaternary ammonium salt compound having long-chain alkyl group, such as trioctylmethyl ammonium chloride (TOMAC).

The salt of a strong acid with a strong base includes, for example sodium chloride, potassium chloride and the like.

The acid includes, for example hydrofluoric acid, hydrochloric acid, hydrobromic acid, sulfuric acid, phosphoric acid, sulphamic acid and the like. These acids become salts in a reaction system.

The acidic catalyst to be used is determined from the viewpoint of the corrosion of autoclaves and the rate of reaction. When trialkylamines are used as a solvent, ammonium chloride is more preferable.

The amount of the acidic catalyst may be 0.1 to 30 parts by weight based on 100 parts by weight of melamine. In order to facilitate the separation of the catalyst and products, the amount is preferably 1 to 5 parts by weight.

Trialkylamines as a solvent includes, for example trialkylamines one alkyl group of which has carbon atoms of 2 to 10. Triethylamine is preferable from the viewpoint of economic efficiency. The amount of the solvent is 10 to 2000 parts by weight, and preferably 50 to 500 parts by weight based on 100 parts by weight of melamine. When the solvent is used in a more amount, the pressure on reaction lowers. However, in such a case the rate of the reaction lowers and thereby the productivity deteriorates.

The removal of ammonia can be carried out by opening gradually a valve of an autoclave to release slowly it, and more efficiently by rectifying under pressure.

The purification of products from a reaction mixture can be carried out by adding gradually the reaction mixture dissolved by heating into a solvent to isolate desired products as slurry. The solvent includes, for example esters, such as ethyl acetate, alcohols, such as methanol or ethanol, ethers, such as cellosorves, dioxane, ethyl ether or isopropyl ether, acetonitrile, DMF, DMSO and NMP, and so on. These solvents may be used alone or in a mixture.

In addition, the slurry obtained by feeding these solvents into an autoclave and then cooling may be filtered to be isolated.

Further, it is easy to purify and isolate the desired products even by solid distillation. In this case, a catalyst to be used should be one having a very high boiling point and high thermal stability.

EXAMPLES

Hereinafter, the present invention is described more specifically on the basis of examples to which the present invention is not limited.

In all of the following Examples, the quantitative determination of products was carried out as follows. First of all, products to be determined were previously synthesized as preparations as indicated in Reference Examples (for example, a method for synthesizing melamine derivatives was processed according to those disclosed in J. Amer. Chem. Soc., 73, 2984 (1951) and U.S. Pat. Nos. 5,124,379 and 4,886,882). Next, a calibration curve was made based on products isolated as pure products and internal standards. Finally, the each amount of products in reaction products was determined by the internal standard quantilative method with high performance liquid chromatography.

The analytical conditions of high performance liquid chromatography used were as follows:
(Analytical Conditions)

Eluting solution: $H_2O/CH_3OH=750/250$ (v/v);

Detection method: UV 220 nm;

Column: lnertsil Ph 150 mm×4.6 mm φ provided by GL Science Co.;

Flow rate: 1.0 ml/min.;

Analytical temperature: 50° C.; and

Internal standard: Parachloroaniline.

(Analyical Conditions: Standard Retention Time (min))
1) Melamine; 3.44;
2) 2,4-diamino-6-methylamino-1,3,5-triazine (mono-type): 4.06;
3) 2-amino-4,6-bis(methylamino)-1,3,5-triazine (bis-type): 5.75;
4) 2,4,6-tris(methylamino)-1,3,5-triazine (tris-type): 10.10; and
5) Parachloroaniline (internal standard): 20.58.

1,3,5-triazine derivatives as preparations were synthesized according to the following Reference Examples.

Reference Example 1

Synthesis of 2,4-diamino-6-chloro-1,3,5-triazine

After 184.5 g (1.0 mol) of cyanuric chloride was dissolved into 800 ml of acelonitrile at a room temperature, the resulting mixture was cooled to 0° C. and 303.7 g (5.0 mol) of 28% aqueous solution of ammonia was added dropwise in 2 hours thereto under vigorous stirring while the reaction temperature was maintained at 10° C. or less. After the adding dropwise was completed, the cooling was stopped, and the mixture was stirred for 1 hour at a room temperature, and then gradually heated to 45° C., and reacted for further 4 hours. After cooling, products were filtered off, and washed with a large amount of water. The resulting filter residue was dried in vacuo at 50° C. for 6 hours to give 115 g (yield: 79%) of the titled compound.

Reference Example 2

Synthesis of 2,4-diamino-6-methylamino-1,3,5-triazine

A mixed solution comprising 14.5 g (0.1 mol) of 2,4-diamino-6-chloro-1,3,5-triazine synthesized in Reference Example 1 and 31.1 g (0.4 mol) of 40% aqueous solution of methylamine was heated under stirring and reacted finally at the reflux temperature thereof for 6 hours. After cooling the reacted solution, products were filtered off, and washed with cold water. The resulting filter residue was dried in vacuo at 70° C. for 6 hours to give 9.1 g (yield: 65%) of the titled compound. Malting point: 269° C.

Reference Example 3

Synthesis of 2,4,6-tris(methylamino)-1,3,5-triazine

After 18.5 g (0.1 mol) of cyanuric chloride was dissolved into 150 ml of acetonitrile, the resulting mixture was cooled to 0° C. and 15.5 g (0.2 mol) of 40% aqueous solution of methylamine was added dropwise in 1 hour thereto under stirring in such a manner that the reaction temperature did not exceed 5° C. While further stirring, 100 ml of water including 20.0 g (0.2 mol) of potassium hydrogencarbonate was added dropwise at the same temperature. Thereafter, the reaction temperature was gradually raised, and stirred at 45° C. for 8 hours. After confirming that an inversion to 2.4-bis(methylamino)-6-chloro-1,3,5-triazine was completed, the reaction solution was cooled and products were filtered off. The filter cake was fully washed with water, and then the resulting 2,4-bis(methylamino)-6-chloro-1,3,5-triazine was suspended into 100 ml of water, and 31.1 g (0.4 mol) of 40% aqueous solution of methylamine was added, and further heated under reflux for 6 hours. After cooling, the deposited crystal was filtered, washed fully with water and dried to give 13.1 g (yield: 78%) of the titled compound. Melting point 133° C.

Reference Example 4

2-amino-4,6-bis(methylamino)-1,3,5-triazine was synthesized similarly to Reference Example 3. Melting point: 291° C.

Example 1

After 5 g of melamine and 0.1 g of ammonium chloride as an acidic catalyst were charged into a 100 ml glass autoclave, a bomb charged with methylamine was connected to the autoclave, and the autoclave was cooled with dry ice-oetone refrigerant. After bubbling from the refrigerant was ceased, 10 g of methylamine in a state of gas was blown into the autoclave from the bomb while weighing with a balance.

Then, the temperature in the autoclave was kept at 190° C. by heating the autoclave. In the course of it, an exothermic reaction occurred from ca. 170° C. In the autoclave, and thereby the temperature was raised by nearly 10° C.

Thereafter, the temperature was raised to 190° C., and thereby the pressure was raised to 10 MPa. The reaction mixture was reacted at 190° C. for 2 hours.

After the reaction was completed, the autoclave was cooled, gaseous materials in the autoclave were removed out of the system by opening a valve, and the autoclave was opened.

The mixture in the autoclave was dissolved in water, and the quantitative analysis thereof was carried out. As a result of it, the degree of conversion of melamine as a raw material was 94.1%, and as products, 2,4-diamino-6-methylamino-1,3,5-triazine, 2-amino-4,6-bis(methylamino)-1,3,5-triazine and 2,4,6-bis(methylamino)-3,5-triazine were prepared in yield of 21.4%, 30.4% and 41.3%, respectively.

Example 2

After 31 g of melamine and 0.5 g of ammonium chloride as an acidic catalyst were charged into a 200 ml glass autoclave, a bomb charged with methylamine was connected to the autoclave, and the autoclave was cooled with dry ice-acetone refrigerant. After bubbling from the refrigerant was ceased, 96 g of methylamine in a state of gas was blown into the autoclave from the bomb while weighing with a balance.

Then, the temperature in the autoclave was kept at 190° C. by heating the autoclave. In the course of it, an exothermic reaction occurred from ca. 170° C. in the autoclave, and thereby the temperature was raised by nearly 10° C. When the temperature was 170° C., the pressure was 6 MPa.

Thereafter, the temperature was raised to 190° C., and thereby the pressure was raised to 11.5 MPa. The reaction mixture was reacted at 190° C. for 1 hour. In this reacton, a valve of the autoclave was loosened, and thereby gas was let out intermittently and gradually, and the reaction was completed at a reaction pressure of 6 MPa. The temperature of the autoclave was raised by a few ° C. each time gas was let out After the reaction was completed, the autoclave was cooled, gaseous materials in the autoclave were removed out of the system by opening a valve, and the autoclave was opened. The color of the interior of autoclave turned into brown. Therefore, corrosion of the autoclave was confirmed.

The mixture in the autoclave was dissolved in water, and the quantitative analysis thereof was carried out. As a result of it, the degree of conversion of melamine as a raw material was 99.8%, and as products, 2,4-diamino-6-methylamino- 1,3,5-triazine, 2-amino-4,6-bis(methylamino)-1,3,5-triazine and 2,4,6-tris(methylamino)-1,3,5-triazine were prepared in yield of 0.9%, 16.1% and 81.0%, respectively.

Example 3

After 31 g of melamine, 10 g of trimethylamine as a solvent and 0.5 g of ammonium chloride as an acidic catalyst were charged into a 200 ml stainless steel autoclave, a bomb charged with methylamine was connected to the autoclave, and the autoclave was cooled with dry ice-acetone refrigerant. After bubbling from the refrigerant was ceased, 63 g of methylamine in a state of gas was blown into the autoclave from the bomb while weighing with a balance.

Then, the temperature in the autoclave was kept at 190° C. by heating the autoclave. In the course of it, an exothermic reaction occurred from ca. 170° C. in the autoclave, and thereby the temperature was raised by nearly 10° C. When the temperature was 170° C., the pressure was 6 MPa.

Thereafter, the temperature was raised to 190° C., and thereby the pressure was raised to 9 MPa. The reaction mixture was reacted at 190° C. for 1 hour.

After the reaction was completed, the autoclave was cooled, gaseous materials in the autoclave were removed out of the system by opening a valve, and the autoclave was opened. No corrosion of the autoclave was confirmed.

The mixture in the autoclave was dissolved in water, and the quantitative analysis thereof was carried out. As a result of it, the degree of conversion of melamine as a raw material was 96.1%, and as products, 2,4-diamino-6-methylamino-1,3,5-triazine, 2-amino-4,6-bis(methylamino)-1,3,5-triazine and 2,4,6-tris(methylamino)-1,3,5-triazine were prepared in yield of 165.5%, 38.2% and 41.0%, respectively.

Example 4

Except that 4 g of triethylamine as a solvent and 0.2 g of sodium chloride as an acidic catalyst were used, the reaction was carried out similarly to the procedures in Example 1.

The mixture in the autoclave was dissolved in water, and the quantitative analysis thereof was carried out. As a result of it, the degree of conversion of melamine as a raw material was 89.3%, and as products, 2,4-diamino-6-methylamino-1,3,5-triazine, 2-amino-4,6-bis(methylamino)-1,3,5triazine and 2,4,6-tris(methylamino)-1,3,5triazine were prepared in yield of 30.9%, 35.8% and 21.7%, respectively.

Example 5

Except that 0.2 g of ammonium sulfate and 0.2 g of potassium chloride as an acidic catalyst were used, the reaction was carried out similarly to the procedures in Example 1.

The mixture in the autoclave was dissolved in water, and the quantitative analysis thereof was carried out. As a result of it, the degree of conversion of melamine as a raw material was 98.8%, and as products, 2,4-diamino-6-methylamino-1,3,5-triazine, 2-amino-4,6-bis(methylamino)-1,3,5-triazine and 2,4,6-tris(methylamino)-1,3,5-triazine were prepared in yield of 17.0%, 49.3% and 32.0%, respectively.

What is claimed is:

1. A process for preparing N-methylated melamines comprising reacting by heating melamine with methylamine in the presence of an acidic catalyst under pressure to substitute at least one amino group of the melamine by methylamino group, wherein an amount of acidic catalyst is 1 to 5 parts by weight based on 100 parts by weight of melamine.

2. The process for preparing N-methylated melamines according to claim 1, wherein the reaction is carried out at a temperature of 160° to 250° C.

3. The process for preparing N-methylated melamines according to claim 1, wherein the reaction is carried out with removal of ammonia generated in the course thereof and thereby increasing the proportion of N-methylated melamines of tris-type and bis-type.

4. A process for preparing N-methylated melamines comprising reacting by heating melamine, methylamine and a solvent in the presence of an acidic catalyst under pressure to substitute at least one amino group of the melamine by methylamino group, wherein an amount of acidic catalyst is 1 to 5 parts by weight based on 100 parts by weight of melamine.

5. The process for preparing N-methylated melamines according to claim 4, wherein the solvent is one or more of trialkylamines.

6. The process for preparing N-methylated melamines according to claim 4, wherein the reaction is carried out at a temperature of 160° to 250° C.

7. The process for preparing N-methylated melamines according to claim 4, wherein the reaction is carried out with removal of ammonia generated in the course thereof and thereby increasing the proportion of N-methylated melamines of tris-type and bis-type.

8. The process for preparing N-methylated melamines according to claim 1, wherein the reaction is carried out under positive pressure.

9. The process for preparing N-methylated melamines according to claim 8, wherein the reaction is carried out at a pressure of 6 to 8 MPa.

10. The process for preparing N-methylated melamines according to claim 1, wherein the reaction is carried out at a pressure of 11 to 12 MPa.

11. The process for preparing N-methylated melamines according to claim 4, wherein the reaction is carried out under positive pressure.

12. The process for preparing N-methylated melamines according to claim 11, wherein the reaction is carried out at a pressure of 4 to 6 MPa.

* * * * *